United States Patent [19]
Merril et al.

[11] Patent Number: 5,811,093
[45] Date of Patent: Sep. 22, 1998

[54] BACTERIOPHAGE GENOTYPICALLY MODIFIED TO DELAY INACTIVATIONS BY THE HOST DEFENSE SYSTEM

[75] Inventors: Carl R. Merril, Rockville, Md.; Richard M. Carlton, Port Washington, N.Y.; Sankar L. Adhya, Gaithersburg, Md.

[73] Assignees: Exponential Biotherapies, Inc., New York, N.Y.; The United States of America as represented by the Department of Health and Human Services, Washington, D.C.

[21] Appl. No.: 631,427

[22] Filed: Apr. 12, 1996

Related U.S. Application Data

[63] Continuation-in-part of Ser. No. 593,269, Jan. 29, 1996, Pat. No. 5,688,501, which is a continuation of Ser. No. 222,956, Apr. 5, 1994, abandoned.

[51] Int. Cl.$^6$ .......................... A01N 63/00; C07H 21/04; C12P 19/34; C12N 7/01
[52] U.S. Cl. .................. 424/93.6; 536/24.33; 435/235.1; 435/91.2
[58] Field of Search .............................. 514/44; 424/93.1, 424/93.2, 93.4, 93.6; 435/172.3, 235.1, 325

[56] References Cited

PUBLICATIONS

H. Williams Smith et al, Journal of General Microbiology, vol. 128, issued 1982, "Successful Treatment of Experimental *Escherichia coli* Infections in Mice using Phage: its General Superiority over Antibiotics", pp. 307–318.

H. Williams Smith et al, Journal of General Microbiology, vol. 133, issued 1987, "The Control of Experimental *Escherichis coli* Diarrhoea in Claves by Means of Bacteriophages", pp. 1111–1126.

*Primary Examiner*—Jasemine C. Chambers
*Assistant Examiner*—Deborah J. R. Clark
*Attorney, Agent, or Firm*—Nikaido Marmelstein Murray & Oram LLP

[57] ABSTRACT

The present invention is directed to bacteriophage therapy, using methods that enable the bacteriophage to delay inactivation by any and all parts of the host defense system (HDS) against foreign objects that would tend to reduce the numbers of bacteriophage and/or the efficiency of those phage at killing the host bacteria in an infection. Disclosed is a method of producing bacteriophage modified for anti-HDS purposes, one method being selection by serial passaging of a bacteriophage, and the other method being genetic engineering of a bacteriophage, so that the modified bacteriophage will remain active in the body for longer periods of time than the wild-type phage.

4 Claims, 4 Drawing Sheets

Fig. 1

λ Major Head Protein (GPE)

Fig. 2A

λ Major Head Protein (GPE) →

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:1:

CCAGCGACGA GACGAAAAAA CG        22

( 2 ) INFORMATION FOR SEQ ID NO:2:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear     ( i i ) MOLECULE TYPE: cDNA     ( x i ) SEQUENCE DESCRIPTION: SEQ ID NO:2:

TTCAGTTGTT CACCCAGCGA GC        22

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( C ) STRANDEDNESS:
        ( D ) TOPOLOGY: linear     ( i i ) MOLECULE TYPE: peptide     ( x i ) SEQUENCE DESCRIPTION: SEQ ID NO:3:

Leu Ala Arg Ser Asn Leu
    1                5

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( C ) STRANDEDNESS:
        ( D ) TOPOLOGY: linear     ( i i ) MOLECULE TYPE: peptide     ( x i ) SEQUENCE DESCRIPTION: SEQ ID NO:4:

Ser Met Tyr Thr Thr Ala Gln Leu Leu Ala Ala Asn Glu Gln Lys
    1              5                        10                    15

( 2 ) INFORMATION FOR SEQ ID NO:5:

( i ) SEQUENCE CHARACTERISTICS:
        ( A ) LENGTH: 16 amino acids
        ( B ) TYPE: amino acid
        ( C ) STRANDEDNESS:
        ( D ) TOPOLOGY: linear     ( i i ) MOLECULE TYPE: peptide     ( x i ) SEQUENCE DESCRIPTION: SEQ ID NO:5:

Met Thr Ser Lys Glu Thr Phe Thr His Tyr Gln Pro Gln Gly Asn Ser
    1              5                        10                    15

( 2 ) INFORMATION FOR SEQ ID NO:6:

(  i  ) SEQUENCE CHARACTERISTICS:
   ( A ) LENGTH: 1600 base pairs
   ( B ) TYPE: nucleic acid
   ( C ) STRANDEDNESS: double
   ( D ) TOPOLOGY: linear (  i i  ) MOLECULE TYPE: DNA (  i x  ) FEATURE:
   ( A ) NAME/KEY: misc_feature
   ( B ) LOCATION: 1..1600

(  x i  ) SEQUENCE DESCRIPTION: SEQ ID NO:6:

| | | | | | |
|---|---|---|---|---|---|
| GCACCACCGA | CGGTGCTGCC | GTTGGCATTC | TTGCGGTTGC | TGCTGACCAG | ACCAGCACCA | 60 |
| CGCTGACGTT | CTACAAGTCC | GGCACGTTCC | GTTATGAGGA | TGTGCTCTGG | CCGGAGGCTG | 120 |
| CCAGCGACGA | GACGAAAAAA | CGGACCGCGT | TGCCGGAAC | GGCAATCAGC | ATCGTTTAAC | 180 |
| TTTACCCTTC | ATCACTAAAG | GCCGCCTGTG | CGGCTTTTTT | TACGGGATTT | TTTTATGTCG | 240 |
| ATGTACACAA | CCGCCCAACT | GCTGGCGGCA | AATGAGCAGA | AATTTAAGTT | TGATCCGCTG | 300 |
| TTTCTGCGTC | TCTTTTTCCG | TGAGAGCTAT | CCCTTCACCA | CGGAGAAAGT | CTATCTCTCA | 360 |
| CAAATTCCGG | GACTGGTAAA | CATGGCGCTG | TACGTTTCGC | CGATTGTTTC | CGGTGAGGTT | 420 |
| ATCCGTTCCC | GTGGCGGCTC | CACCTCTGAA | TTTACGCCGG | GATATGTCAA | GCCGAAGCAT | 480 |
| GAAGTGAATC | CGCAGATGAC | CCTGCGTCGC | CTGCCGGATG | AAGATCCGCA | GAATCTGGCG | 540 |
| GACCCGGCTT | ACCGCCGCCG | TCGCATCATC | ATGCAGAACA | TGCGTGACGA | AGAGCTGGCC | 600 |
| ATTGCTCAGG | TCGAAGAGAT | GCAGGCAGTT | TCTGCCGTGC | TTAAGGGCAA | ATACACCATG | 660 |
| ACCGGTGAAG | CCTTCGATCC | GGTTGAGGTG | GATATGGGCC | GCAGTGAGGA | GAATAACATC | 720 |
| ACGCAGTCCG | GCGGCACGGA | GTGGAGCAAG | CGTGACAAGT | CCACGTATGA | CCCGACCGAC | 780 |
| GATATCGAAG | CCTACGCGCT | GAACGCCAGC | GGTGTGGTGA | ATATCATCGT | GTTCGATCCG | 840 |
| AAAGGCTGGG | CGCTGTTCCG | TTCCTTCAAA | GCCGTCAAGG | AGAAGCTGGA | TACCCGTCGT | 900 |
| GGCTCTAATT | CCGAGCTGGA | GACAGCGGTG | AAAGACCTGG | GCAAAGCGGT | GTCCTATAAG | 960 |
| GGGATGTATG | GCGATGTGGC | CATCGTCGTG | TATTCCGGAC | AGTACGTGGA | AAACGGCGTC | 1020 |
| AAAAAGAACT | TCCTGCCGGA | CAACACGATG | GTGCTGGGGA | ACACTCAGGC | ACGCGGTCTG | 1080 |
| CGCACCTATG | GCTGCATTCA | GGATGCGGAC | GCACAGCGCG | AAGGCATTAA | CGCCTCTGCC | 1140 |
| CGTTACCCGA | AAAACTGGGT | GACCACCGGC | GATCCGGCGC | GTGAGTTCAC | CATGATTCAG | 1200 |
| TCAGCACCGC | TGATGCTGCT | GGCTGACCCT | GATGAGTTCG | TGTCCGTACA | ACTGGCGTAA | 1260 |
| TCATGGCCCT | TCGGGGCCAT | TGTTTCTCTG | TGGAGGAGTC | CATGACGAAA | GATGAACTGA | 1320 |
| TTGCCCGTCT | CCGCTCGCTG | GGTGAACAAC | TGAACCGTGA | TGTCAGCCTG | ACGGGACGA | 1380 |
| AAGAAGAACT | GGCGCTCCGT | GTGGCAGAGC | TGAAAGAGGA | GCTTGATGAC | ACGGATGAAA | 1440 |
| CTGCCGGTCA | GGACACCCCT | CTCAGCCGGG | AAAATGTGCT | GACCGGACAT | GAAAATGAGG | 1500 |
| TGGGATCAGC | GCAGCCGGAT | ACCGTGATTC | TGGATACGTC | TGAACTGGTC | ACGGTCGTGG | 1560 |
| CACTGGTGAA | GCTGCATACT | GATGCACTTC | ACGCCACGCG | | | 1600 |

BACTERIOPHAGE GENOTYPICALLY MODIFIED TO DELAY INACTIVATIONS BY THE HOST DEFENSE SYSTEM

This application is a continuation-in-part of application Ser. No. 08/593,269, filed Jan. 29, 1996, now U.S. Pat. No. 5,688,501, which is a continuation of application Ser. No. 08/222,956, filed Apr. 5, 1994, now abandoned.

FIELD OF THE INVENTION

The present invention relates to a method of delaying the inactivation of bacteriophages by an animal's host defense system. One method of delaying inactivation is the use of novel bacteriophages whose genomes have been modified. Methods useful for modifying the bacteriophage genome include but are not limited to selection of mutant strains by serial passage, and the creation of new strains by genetic engineering. Such novel bacteriophages have the ability to delay being sequestered by, engulfed by, or otherwise inactivated by one or more of the processes of an animal's host defense system (HDS). This novel attribute allows the "anti-HDS modified" bacteriophage to have a longer survival time in an animal's body than the corresponding wild-type bacteriophage, and that in turn allows the modified phage to be more effective than the wild-type phage at treating (or assisting in the treatment of) a bacterial infection.

The present invention also is directed to specific methods of using bacteriophages for treating infectious bacterial diseases. The route of administration can be by any means including delivering the phage by aerosol to the lungs.

BACKGROUND OF THE INVENTION

In the 1920s, shortly after the discovery of bacterial viruses (bacteriophages), the medical community began to extensively pursue the treatment of bacterial diseases with bacteriophage therapy. The idea of using phage as a therapy for infectious bacterial diseases was first proposed by d'Herelle in 1918, as a logical application of the bacteriophages' known ability to invade and destroy bacteria. Although early reports of bacteriophage therapy were somewhat favorable, with continued clinical usage it became clear that this form of therapy was inconsistent and unpredictable in its results. Disappointment with phage as a means of therapy grew, because the great potential of these viruses to kill bacteria in vitro was not realized in vivo. This led to a decline in attempts to develop clinical usage of phage therapy, and that decline accelerated once antibiotics began to be introduced in the 1940s and 50s. From the 1960s to the present, some researchers who adopted certain bacteriophages as a laboratory tool and founded the field of molecular biology have speculated as to why phage therapy failed.

Despite the general failure of phage as therapy, isolated groups of physicians have continued to try to use these agents to treat infectious diseases. Many of these efforts have been concentrated in Russia and India, where the high costs of and lack of availability of antibiotics continues to stimulate a search for alternative therapies. See for example Vogovazova et al., "Effectiveness of *Klebsiella pneumoniae* Bacteriophage in the Treatment of Experimental Klebsiella Infection", *Zhurnal Mikrobiologii, Epidemiologii Immunobiologii,* pp. 5–8 (April, 1991); and Vogovazova et al., "Immunological Properties and Therapeutic Effectiveness of Preparations of Klebsiella Bacteriophages", *Zhurnal Mikrobiologii, Epidemiologii Immunobiologii,* pp. 30–33 (March, 1992)]. These articles are similar to most of the studies of phage therapy, including the first reports by d'Herelle, in that they lack many of the controls required by researchers who investigate anti-infectious therapies. In addition, these studies often have little or no quantification of clinical results. For example, in the second of the two Russian articles cited above, the Results section concerning Klebsiella phage therapy states that "Its use was effective in . . . ozena (38 patients), suppuration of the nasal sinus (5 patients) and of the middle ear (4 patients) . . . In all cases a positive clinical effect was achieved without side effects from the administration of the preparation". Unfortunately, there were no placebo controls or antibiotic controls, and no criteria were given for "improvement".

Another clinical use of phage that was developed in the 1950s and is currently still employed, albeit to a limited extent, is the use of phage lysate, specifically staphphage lysate (SPL). The researchers in this field claim that a nonspecific, cell-mediated immune response to staph endotoxin is an integral and essential part of the claimed efficacy of the SPL. [See, eg., Esber et al., J. Immunopharmacol., Vol. 3, No. 1, pp. 79–92 (1981); Aoki et al., Augmenting Agents in Cancer Therapy (Raven, N.Y.), pp. 101–112 (1981); and Mudd et al., Ann. NY Acad. Sci., Vol. 236, pp. 244–251 (1974).] In this treatment, it seems that the purpose of using the phage is to lyse the bacteria specifically to obtain bacterial antigens, in a manner that those authors find preferential to lysing by sonication or other physical/chemical means. Here again, some difficulties arise in assessing these reports in the literature, because, in general, there are no placebo controls and no standard antibiotic controls against which to measure the reported efficacy of the SPL. More significantly, there is no suggestion in these articles to use phage per se in the treatment of bacterial diseases. Moreover, the articles do not suggest that phage should be modified in any manner that would delay the capture/sequestration of phage by the host defense system.

Since many patients will recover spontaneously from infections, studies must have carefully designed controls and explicit criteria to confirm that a new agent is effective. The lack of quantification and of controls in most of the phage reports from d'Herelle on makes it difficult if not impossible to determine if the phage therapies have had any beneficial effect.

As there are numerous reports of attempts at phage therapy, one would assume that had it been effective, it would have flourished in the period before antibiotics were introduced. But phage therapy has been virtually abandoned, except for the isolated pockets mentioned above.

As noted above, some of the founders of molecular biology who pioneered the use of specific phages to investigate the molecular basis of life processes have speculated as to why phage therapy was not effective. For example, G. Stent in his book *Molecular Biology of Bacterial Viruses,* WH Freeman & Co. (1963) pp. 8–9, stated the following:

"Just why bacteriophages, so virulent in their antibiotic action in vitro, proved to be so impotent in vivo, has never been adequately explained. Possibly the immediate antibody response of the patient against the phage protein upon hypodermic injection, the sensitivity of the phage to inactivation by gastric juices upon oral administration, and the facility with which bacteria acquire immunity or sport resistance against phage, all militated against the success of phage therapy."

In 1973, one of the present inventors, Dr. Carl Merril, discovered along with his coworkers that phage lambda, administered by various routes (per os, IV, IM, IP) to germ-free, non-immune mice, was cleared out of the blood stream very rapidly by the organs of the reticulo-endothelial system, such as the spleen, liver and bone marrow. [See Geier, Trigg and Merril, "Fate of Bacteriophage Lambda in Non-Immune, Germ-Free Mice", *Nature,* 246, pp. 221–222 (1973).] These observations led Dr. Merril and his co-workers to suggest (in that same *Nature* article cited above) over-coming the problem by flooding the body with colloidal particles, so that the reticulo-endothelial system would be so overwhelmed engulfing the particles that the phage might escape capture. Dr. Merril and his coworkers did not pursue that approach at the time as there was very little demand for an alternative antibacterial treatment such as phage therapy in the 1970s, given the numerous and efficacious antibiotics available.

Subsequently, however, numerous bacterial pathogens of great importance to mankind have become multi-drug resistant (MDR), and these MDR strains have spread rapidly around the world. As a result, hundreds of thousands of people now die each year from infections that could have been successfully treated by antibiotics just 4–5 years ago. [See e.g. C. Kunin, "Resistance to Antimicrobial Drugs—A Worldwide Calamity", Annals of Internal Medicine, 1993;118: 557–561; and H. Neu, "The Crisis in Antibiotic Resistance", *Science* 257, 21 Aug 1992, pp. 1064–73.] In the case of MDR tuberculosis, e.g., immunocompromised as well as non-immunocompromised patients in our era are dying within the first month or so after the onset of symptoms, despite the use of as many as 11 different antibiotics.

Medical authorities have described multi-drug resistance not just for TB, but for a wide variety of other infections as well. Some infectious disease experts have termed this situation a "global crisis". A search is underway for alternative modes and novel mechanisms for treating these MDR bacterial infections.

Bacteriophage therapy offers one possible alternative treatment. Learning from the failure of bacteriophage therapy in the past, the present inventors have discovered effective ways to overcome the major obstacles that were the cause of that failure.

One object of the present invention is to develop novel bacteriophages which are able to delay inactivation by an animal's host defense system, any component of which may be diminishing the numbers or the efficacy of the phage that have been administered.

Another object of the present invention is to develop a method for treating bacterial infectious diseases in an animal by administering to the animal an effective amount of the novel bacteriophage, and by an appropriate route of administration.

SUMMARY OF THE INVENTION

In the present invention, novel bacteriophages are developed by serial passage or by genetic engineering, to obtain bacteriophages capable of delaying inactivation by any component of an animal's host defense system (HDS) against foreign bodies. This allows the novel phages to survive for longer periods of time in the circulation and the tissues than the wild-type phage, thereby prolonging viability and making these modified phages more efficient at reaching and invading the bacteria at the site of an infection.

The administration of an anti-HDS phage that has been developed by serial passage or by genetic engineering will enable the animal recipient to efficaciously fight an infection with the corresponding bacterial pathogen. The phage therapy of this invention will therefore be useful either as an adjunct to standard anti-infective therapies, or as a stand-alone therapy.

The phages of the present invention can be administered by any route, such as oral, pulmonary (by aerosol or by other respiratory device for respiratory tract infections), nasal, IV, IP, per vagina, per rectum, intra-ocular, by lumbar puncture, intrathecal, and by burr hole or craniotomy if need be for direct insertion onto the meninges (e.g. in a heavily thickened and rapidly fatal tuberculous meningitis).

BRIEF DESCRIPTION OF THE DRAWINGS

FIG. 3 shows a comparison of the efficacy of the wild-type λvir to that of the selected long-circulating strains Argo1 and Argo2, as therapeutic agents for the treatment of bacteremia caused by the IP injection of *E. coli* CRM1 into Balb/c female mice. All of the mice were injected IP with a lethal dose of *E. coli* CRM1 ($2\times10^8$ colony forming units). Thirty minutes later the mice in group 2 (■) received an IP injection if λvir and the mice in group 3 (●) received an IP injection of Argo1. Mice in group 1 (▲) did not receive any phage. A fourth group treated with Argo2 produced results indistinguishable from those observed with Argo1. The mice were observed and rated according to their condition for a period of 100 hours: 0=normal mouse; 1=decreased activity and ruffled fur; 2=lethargy, ruffled fur and hunchback posture; 3=lethargy, ruffled fur, hunchback posture and partially closed eyes with exudate around the eyes; 4=moribund; 5=death. As the observations are categorical condition-stage observations, the actual distances between the states is unknown. For this reason, the level of illness indicated in this illustration is provided simply to record the progression of the disease state. In addition, there was no significant variation of symptoms within any of the experimental groups.

DETAILED DESCRIPTION OF THE INVENTION

One of the major obstacles to bacteriophage therapy is the fact that when phages are administered to animals, they are rapidly eliminated by the animal's HDS. That suggests that the phages are not viable in the animal's circulation or tissues for a long enough time to reach the site of infection and invade the bacteria. Thus, the object of the present invention is to develop bacteriophages that are able to delay inactivation by the HDS. This will prolong phage viability in the body.

The term "host defense system" as used herein refers to all of the various structures and functions that help an animal to eliminate foreign bodies. These defenses include but are not limited to the formed cells of the immune system and the humoral components of the immune system, those humoral components including such substances as complement, lysozymes and beta-lysin. In addition, the organs of what has often been referred to as the "reticulo-endothelial system" (spleen, liver, bone marrow, lymph glands, etc.) also serve as part of the host defense system. In addition to all the phenomena cited just above which take place within this "reticulo-endothelial system", there has also been described a sequestering action wherein foreign materials (specifically including bacteriophage) are captured non-phagocytically and non-destructively in the spleen by what is known as the Schweigger-Seidel capillary sheaths—a phenomenon that may or may not involve antigen capture [See e.g. Nagy, Z., Horrath, E., and Urban, Z., Nature New Biology, 242: p. 241 (1973).]

The phrase "substantially eliminate" as used regarding the present invention, indicates that the number of bacteria is reduced to a number which can be completely eliminated by the animal's defense system or by using conventional antibacterial therapies.

Enabling bacteriophages to delay inactivation by those host defense systems—whichever components of it may or may not be employed in any given case—would be likely to result in an increased in vivo killing of bacterial pathogens that are in the host range for those bacteriophages.

In one embodiment, bacteriophages are selected by serial passage. These will by their nature have a delay in their inactivation by the HDS. Essentially, the serial passage is accomplished by administering the phage to an animal and obtaining serial blood samples over an extended period of time. Eventually one obtains viable phage that are able to delay inactivation by the HDS. When a period is reached where in blood samples there remains 0.01%–1.0%, and preferably 0.1%, of the number of phages originally placed in circulation, a sample of this remaining phage is grown up to sufficiently high titer to be injected into a second animal of the same species. [For methods of clonal purification, see M. Adams, *Bacteriophages,* Interscience Publishers, pp. 454–460 (1959)]. Serial blood samples are again obtained over time, and the process described above is repeated iteratively so that each time when approximately 0.1% of the phages are left, it takes longer and longer with each serial passage to reach that point when only 0.1% of the phage administered still remain in circulation. By this method of clonal purification and selection, a phage strain will be isolated that can survive at least 15% longer in the body than the longest-surviving wild-type phage.

After a number of serial passages of these non-mutagenized or mutagenized (see below) bacteriophage, a prototype "anti-HDS modified" bacteriophage is obtained. As used herein, an "anti-HDS modified" phage is defined as any phage (whether modified by serial passage or by genetic engineering) that has a half-life within the animal that is at least 15% greater than the half-life of the original wild-type phage from which it was derived. Half-life refers to the point in time when out of an initial IV dose (e.g. $1 \times 10^{12}$) of a given phage, half ($5 \times 10^{11}$) of them still remain in circulation, as determined by serial pfu experiments ("pfu" meaning plaque forming units, a convenient measure of how many phage are present in a given sample being assayed). A 15% longer half-life indicates a successful delay of inactivation by the HDS.

The evidence that the HDS-evading phages do in fact remain viable for a longer period of time in the body is obtained by demonstrating not only by the longer time that they remain in the circulation, but also by the higher numbers of them that remain in the circulation at a given point in time. This slower rate of clearance is demonstrated by the fact that ten minutes after the IV injection of $1 \times 10^{12}$ of the phages into a test animal, the number of the phages still in circulation (as measured by pfu assays) is at least 10% higher than the number of the corresponding wild-type phage still in circulation in the control animal, at that point in time.

Instead of awaiting the spontaneous mutations that are selected for in the above method, alternatively mutations can be provoked during the growth of the phage in its host bacteria. The mutations may produce specimens of phage that, after selection by serial passage, are even more efficient than the non-mutagenized phage at delaying inactivation by the host defense system. Mutagenization is achieved by subjecting the phage to various stimuli, such as, but not limited to, acridine compounds, ethidium bromide in the presence of light, radioactive phosphorus, and various forms of radiation (X-rays, UV light, etc.). Mutants resulting from the iterative procedure described above, and that are found to have a longer survival time than the wild-type phage, are grown to high titer and are used to treat infectious diseases in animals and in humans.

The phage obtained by the above methods are referred to as "anti-HDS selected".

An altogether different method to achieve the desired result is to genetically engineer a phage so that it expresses molecules on its surface coat, where said molecules antagonize, inactivate, or in some other manner impede those actions of the HDS that would otherwise reduce the viability of the administered phages. One of the ways to accomplish this is to engineer a phage to express molecules that antagonize one or more of the complement components.

Complement components fix to bacteriophages, and these bacteriophages then adhere to certain white blood cells (such as macrophages) that express complement receptors. Numerous peptides have been synthesized that antagonize the functions of the various complement components. [See e.g. Lambris, J. D. et al, "Use of synthetic peptides in exploring and modifying complement reactivities" in *Activators and Inhibitors of Complement,* ed. R. Sim, Kluwer Academic Publishers, Boston, 1993.] Lambris et al. (op.cit.) cite "a series of synthetic peptides spanning the convertase cleavage site in C3 (that are) found to inhibit complement activation by both the classical and alternative pathways". Among the peptides cited is a six amino acid peptide (LARSNL (SEQ ID NO: 3), residues 746–751 of C3) that "inhibits both pathways equally well".

In one method of genetically engineering such a phage, a fusion protein is obtained, wherein the peptide will be bound to the carboxyl end of the surface protein of interest [See e.g. Sambrook, J., Fritsch, E., and Maniatis, T.: Molecular Cloning. A Laboratory Manual, 2nd Ed., Cold Spring Harbor Laboratory Press, Cold Spring Harbor, N.Y., 1989]. This construct is made by cloning the gene for the phage surface protein into a plasmid vector system, and then cloning the oligonucleotide for the peptide of interest into this carrying vector by in-frame fusion at the 3'-end of the gene for the surface protein. This fusion of the gene for the phage surface protein with the oligonucleotide for the complement-antagonizing peptide would then be incorporated into the phage of interest by the in vivo generalized recombination system in the host bacteria for the phage of interest. Phage whose genomic sequence is already completely known, and phage whose genomic sequence is unknown or partially unknown can be used in the present invention.

The surface expression of a recombinant complement-antagonizing peptide is but one example of several complement-related strategies that might be used for these purposes. Another example would be the expression of a human complement-antagonizing protein on the surface of a phage. Several transplantation research facilities are currently expressing such human complement-antagonizing proteins in transgenic animals, in the hopes that when these transgenic organs are donated they will not be immunologically rejected by a human recipient. [See e.g. Genetic Engineering News, Oct. 15, 1993, p.1.] In an analogous manner, the expression of such recombinant human complement-antagonizing proteins on the surface of a bacteriophage may allow the phage to delay being inactivated by the host defense system.

In addition to complement-related strategies, there are many other categories of molecules that can be recombinantly engineered into a phage to delay inactivation by the host's defense system. Other categories of molecules that could be expressed on the surface of bacteriophages, and would fall under the scope of this invention, include but are not limited to: interleukins and other cytokines; autocrines; and inhibitors of the various cellular activating or inhibiting factors (e.g. inhibitors of macrophage activating factor). Genes for these proteins (or for active subunits of them) can be incorporated into a phage genome so that they will be expressed on the surface.

In addition, if it were possible to get a given bacterial host strain to glycosylate a recombinant protein, then the purpose of the invention could be served by introducing genes that will express glycosylated proteins. Such proteins are known by their negative charge to repel immune cells, such as the macrophage. Examples might include but would not be limited to (1) the C-terminal portion of the β-subunit of human chorionic gonadotrophin (hCG), and (2) the various glycophorins on the surfaces of blood cells.

Phage modified in this manner are referred to as "anti-HDS engineered".

The present invention can be applied across the spectrum of bacterial diseases, either by serial passage of phages (mutagenized or non-mutagenized) or by genetically engineering phages, so that phages are developed that are specific for each of the bacterial strains of interest. In that way, a full array of anti-HDS selected and/or anti-HDS engineered bacteriophage is developed for virtually all the bacterial (and other applicable) pathogens for man, his pets, livestock and zoo animals (whether mammal, avian, or pisciculture). Phage therapy will then be available:

1) as an adjunct to or as a replacement for those antibiotics and/or chemotherapeutic drugs that are no longer functioning in a bacteriostatic or bactericidal manner due to the development of multi-drug resistance;
2) as a treatment for those patients who are allergic to the antibiotics and/or chemotherapeutic drugs that would otherwise be indicated; and
3) as a treatment that has fewer side effects than many of the antibiotics and/or chemotherapeutic drugs that would otherwise be indicated for a given infection.

The second embodiment of the present invention is the development of methods to treat bacterial infections in animals through phage therapy with the anti-HDS modified bacteriophages described above. Hundreds of bacteriophages and the bacterial species they infect are known in the art. The present invention is not limited to a specific bacteriophage or a specific bacteria. Rather, the present invention can be utilized to develop anti-HDS modified bacteriophages which can be used to treat any and all infections caused by their host bacteria.

While it is contemplated that the present invention can be used to treat any bacterial infection in an animal, it is particularly contemplated that the methods described herein will be very useful as a therapy (adjunctive or stand-alone) in infections caused by drug-resistant bacteria. Experts report [See e.g. Gibbons, A., "Exploring New Strategies to Fight Drug-Resistant Microbes, *Science,* 21 Aug. 1993, pp. 1036–38.] that at the present time, the drug-resistant bacterial species and strains listed below represent the greatest threat to mankind:

1. All of the clinically important members of the family Enterobacteriaceae, most notably but not limited to the following:
   a) All the clinically important strains of Escherichia, most notably *E. coli.* One among a number of candidate wild-type phages against these particular pathogens that could be used as a starting point for the serial passage and/or the genetic engineering of the present invention would be ATCC phage # 23723-B2. [Note: For purposes of brevity, in all the following examples of pathogens, the corresponding wild-type phage will be indicated by the following phraseology: "Example of corresponding phage:_____."]
   b) All the clinically important strains of Klebsiella, most notably *K. pneumoniae* [Example of corresponding phage: ATCC phage # 23356-B1].
   c) All the clinically important strains of Shigella, most notably *S. dysenteriae* [Example of corresponding phage: ATCC phage # 11456a-B1].
   d) All the clinically important strains of Salmonella, including *S. abortus-equi* [Example of corresponding phage: ATCC phage # 9842-B1], *S. typhi* [Example of corresponding phage: ATCC phage # 19937-B1], *S. typhimurium* [*Example of corresponding phage: ATCC phage* # 19585-B1], *S. newport* [Example of corresponding phage: ATCC phage # 27869-B1], *S. paratyphi-A* [Example of corresponding phage: ATCC phage # 12176-B1], *S. paratyphi-B* [Example of corresponding phage: ATCC phage # 19940-B1], *S. potsdam* [Example of corresponding phage: ATCC phage # 25957-B2], and *S. pollurum* [Example of corresponding phage: ATCC phage # 19945-B1].
   e) All the clinically important strains of Serratia, most notably *S. marcescens* [Example of corresponding phage: ATCC phage # 14764-B1].
   f) All the clinically important strains of Yersinia, most notably *Y. pestis* [Example of corresponding phage: ATCC phage # 11953-B1].
   g) All the clinically important strains of Enterobacter, most notably *E. cloacae* [Example of corresponding phage: ATCC phage # 23355-B1].
2. All the clinically important Enterococci, most notably *E. faecalis* [Example of corresponding phage: ATCC phage

19948-B1] and *E. faecium* [Example of corresponding phage: ATCC phage #19953-B1].

3. All the clinically important Haemophilus strains, most notably *H. influenzae* [a corresponding phage is not available from ATCC for this pathogen, but several can be obtained from WHO or other labs that make them available publicly].
4. All the clinically important Mycobacteria, most notably *M. tuberculosis* [Example of corresponding phage: ATCC phage # 25618-B1], *M. avium-intracellulare, M. bovis,* and *M. leprae.* [Corresponding phage for these pathogens are available commercially from WHO, via The National Institute of Public Health & Environmental Protection, Bilthoven, The Netherlands].
5. *Neisseria gonorrhoeae* and *N. meningitidis* [Corresponding phage for both can be obtained publicly from WHO or other sources].
6. All the clinically important Pseudomonads, most notably *P. aeuruginosa* [Example of corresponding phage: ATCC phage # 14203-B1].
7. All the clinically important Staphylococci, most notably *S. aureus* [Example of corresponding phage: ATCC phage # 27690-B1] and *S. epidermidis* [Corresponding phage are available publicly through the WHO, via the Colindale Institute in London].
8. All the clinically important Streptococci, most notably *S. pneumoniae* [Corresponding phage can be obtained publicly from WHO or other sources].
9. *Vibrio cholera* [Example of corresponding phage: ATCC phage # 14100-B1].

There are additional bacterial pathogens too numerous to mention that, while not currently in the state of antibiotic-resistance crisis, nevertheless make excellent candidates for treatment with anti-HDS modified bacteriophages that are able to delay inactivation by the HDS, in accordance with the present invention. Thus, all bacterial infections caused by bacteria for which there is a corresponding phage can be treated using the present invention.

Any phage strain capable of doing direct or indirect harm to a bacteria (or other pathogen) is contemplated as useful in the present invention. Thus, phages that are lytic, phages that are lysogenic but can later become lytic, and nonlytic phages that can deliver a product that will be harmful to the bacteria are all useful in the present invention.

The animals to be treated by the methods of the present invention include but are not limited to man, his domestic pets, livestock, pisciculture, and the animals in zoos and aquatic parks (such as whales and dolphins).

The anti-HDS modified bacteriophage of the present invention can be used as a stand-alone therapy or as an adjunctive therapy for the treatment of bacterial infections. Numerous antimicrobial agents (including antibiotics and chemotherapeutic agents) are known in the art which would be useful in combination with anti-HDS modified bacteriophage for treating bacterial infections. Examples of suitable antimicrobial agents and the bacterial infections which can be treated with the specified antimicrobial agents are listed below. However, the present invention is not limited to the antimicrobial agents listed below as one skilled in the art could easily determine other antimicrobial agents useful in combination with anti-HDS modified bacteriophage.

| Pathogen | Antimicrobial or antimicrobial group |
|---|---|
| *E. coli* | trimethoprim-sulfamethoxazole |
| -uncomplicated urinary tract infection | (abbrev. TMO-SMO), or ampicillin; 1st generation cephalosporins, ciprofloxacin |
| -systemic infected | ampicillin, or a 3rd generation cephalosprorin; aminoglycosides, aztreonam, or a penicillin + a penicillinase inhibitor |
| *Klebsiella pneumonia* | 1st generation cephalosporins; 3rd gener. cephalosporins, cefotaxime, moxalactam, amikacin, chloramphenicol |
| *Shigella* (various) | ciprofloxacin; TMO-SMO, ampicillin, chloramphenicol |
| Salmonella: | |
| -*S. typhi* | chloramphenicol; ampicillin or TMO-SMO |
| -non-typhi species | ampicillin; chloramphenicol, TMO-SMO, ciprofloxacin |
| *Yersinia pestis* | streptomycin; tetracycline, chloramphenicol |
| *Enterobacter cloacae* | 3rd generation cephalosporins,, gentamicin, or tobramycin; carbenicillin, amikacin, aztreonam, imipenem |
| *Hemophilus influenzae:* | |
| -meningitis | chloramphenicol or 3rd generation cephalosporins; ampicillin |
| -other *H. infl.* infections | ampicillin; TMO-SMO cefaclor, cefuroxime, ciprofloxacin |
| *Myobacterium tuberculosis* and *M. avium-intracellulare* | isoniazid (INH) + rifampin or rifabutin, the above given along with pyrazinamide +/or ethambutol |
| Neisseria: | |
| -*N. meningitidis* | penicllin G; chloramphenicol, or a sulfonamide |
| -*N. gonorrhoeae:* | |
| penicillin-sensitive | penicillin G; spectinomycin, ceftriaxone |
| penicillin-resistant | ceftriaxone; spectinomycin, cefuroxime or cefoxitin, ciprofloxacin |
| *Pseudomonas aeruginosa* | tobramycin or gentamycin (+/- carbenicillin, aminoglycosides); amikacin, cefazidime, aztreonam, imipenem |
| *Staph aureus* | |
| -non-penicillinase producing | penicillin G; 1st generation cephalosporins, vancomycin, imipenem, erythromycin |
| -penicillinase producing | a penicillinase-resisting penicillin; 1st generation cephalosporins, vancomycin, imipenem, erythrommycin |
| *Streptococcus pneumoniae* | penicillin G; 1st generation cephalosproins, erythromycin, chloramphenicol |
| *Vibrio cholera* | tetracycline; TMO-SMO |

The routes of administration include but are not limited to: oral, aerosol or other device for delivery to the lungs, nasal spray, intravenous, intramuscular, intraperitoneal, intrathecal, vaginal, rectal, topical, lumbar puncture, intrathecal, and direct application to the brain and/or meninges. Excipients which can be used as a vehicle for the delivery of the phage will be apparent to those skilled in the art. For example, the free phage could be in lyophilized form and be dissolved just prior to administration by IV injection. The dosage of administration is contemplated to be in the range of about $10^6$ to about $10^{13}$ pfu/per kg/per day, and preferably about $10^{12}$ pfu/per kg/per day. The phage are administered until successful elimination of the pathogenic bacteria is achieved.

With respect to the aerosol administration to the lungs, the anti-HDS modified phage is incorporated into an aerosol formulation specifically designed for administration to the lungs by inhalation. Many such aerosols are known in the art, and the present invention is not limited to any particular formulation. An example of such an aerosol is the Proventil™ inhaler manufactured by Schering-Plough, the propellant of which contains trichloromonofluoromethane, dichlorodifluoromethane and oleic acid. The concentrations of the propellant ingredients and emulsifiers are adjusted if necessary based on the phage being used in the treatment. The number of phage to be administered per aerosol treatment will be in the range of $10^6$ to $10^{13}$ pfu, and preferably $10^{12}$ pfu.

The foregoing embodiments of the present invention are further described in the following Examples. However, the present invention is not limited by the Examples, and variations will be apparent to those skilled in the art without departing from the scope of the present invention. In particular, any bacteria and phage known to infect said bacteria can be substituted in the experiments of the following examples.

EXAMPLES

Example 1

Selection of anti-HDS selected phage by serial passage through mice. Part 1. A stock of mutagenized or non-mutagenized lambda coliphage strain is injected in one bolus into the blood of laboratory mice at $10^{12}$ pfu/per kg, suspended in 0.5 cc of sterile normal saline. The mice are periodically bled to follow the survival of the phage in the body. The phage are assayed by plating them on their laboratory host, *E. coli.* When the titer of phage in the mice reaches a range of 0.01%–1.0%, and preferably 0.1%, of the titer initially injected, the phage isolated at this point in time are plaque isolated and the procedure repeated. The repeated passage of the lambda phage between animal and bacteria yields a phage strain that has a longer survival time in the body of the mice. The anti-HDS selected phage strain is then subjected to clonal (plaque) purification.

Where the phage being administered for serial passage have first been mutagenized, the mutagenization is carried out according to procedures known in the art [See e.g., Adams, M. *Bacteriophages.* NY: Wiley Interscience, 1959, pp. 310–318 and pp. 518–520.] For mutagenization by ultraviolet radiation, during the last 40%–90% (and preferably 65%) of the latent period, the phage (inside the infected host bacteria) are exposed to 3,000–6,000 ergs (and preferably 4,500 ergs) of ultraviolet radiation per square mm. For mutagenization by X-radiation, a wavelength of 0.95 Å is used at doses from 10–250 (and preferably 150) kiloroentgens.

Example 2

Determination that HDS inactivation is delayed for the Anti-HDS Selected Phage as compared to Wild-Type Phage.

Two groups of mice are injected with phage as specified below:

Group 1: The experimental group receives an IV injection consisting of $1\times10^{12}$ of the anti-HDS selected phage, suspended in 0.5 cc of normal sterile saline.

Group 2: The control group receives a parenteral injection consisting of $1\times10^{12}$ of the wild-type phage from which the serially-passaged phage were derived, suspended in 0.5 cc of sterile normal saline.

Both groups of mice are bled at regular intervals, and the blood samples assayed for phage content (by pfu assays) to determine the following:

1) Assays for half-lives of the two phages: For each group of mice, the point in time is noted at which there remains in circulation only half (i.e., $5\times10^{11}$) the amount of phage as administered at the outset. The point in time at which half of the anti-HDS selected phage have been eliminated from the circulation is at least 15% longer than the corresponding point in time at which half of the wild-type phage have been eliminated from the circulation.
2) Assays for absolute numbers: For each group of mice, a sample of blood is taken at precisely 1 hour after administration of the phage. At 1 hour post-injection, the numbers of anti-HDS-selected phage in circulation are at least 10% higher than the numbers of wild-type phage still in circulation.

Example 3

Determination that the anti-HDS selected phage has a greater capacity than wild-type phage to prevent lethal infections in mice.

Part 1. Peritonitis Model: An $LD_{100}$ dosage of *E. coli* is administered intraperitonally (IP) to laboratory mice. The strain of *E. coli* used is known to be lysed by the coliphage strain that is selected by Serial Passage. The treatment modality is administered precisely 20 minutes after the bacteria are injected, but before the onset of symptoms. The treatment modalities consist of the following:

Group 1: The experimental group receives an IP injection consisting of $1\times10^{12}$ of the anti-HDS selected phage lambda coliphage suspended in 0.5 cc of sterile normal saline.

Group 2: A first control group receives an IP injection consisting of $1\times10^{12}$ of the wild-type phage from which the anti-HDS selected phage were developed, suspended in 0.5 cc of normal sterile saline.

Group 3: A second control group receives an IP injection of 0.5 cc normal sterile saline.

Evidence that treatment with the anti-HDS selected phage prevented the development of a lethal event in the peritonitis model is measured by using the following three criteria:

(1) Survival of the animal
(2) Bacterial counts: Samples of peritoneal fluid are withdrawn every ½ hour from the three groups of infected mice, and the rate of increase or decrease in *E. coli* colony counts in the three groups is noted
(3) Phage control: Using the samples of IP fluid withdrawn from the infected mice, the numbers of pfu of the anti-HDS selected phage and the numbers of pfu of the wild-type phage are noted.

Part 2. Bacteremia Model:

An $LD_{100}$ dosage of *E. coli* is administered parenterally to laboratory mice, where the strain of *E. coli* used is known to be lysed by the coliphage strain that was chosen for the serial passage. The treatment modality (see below) is administered precisely 20 minutes after the bacteria are injected, but before the onset of symptoms. The treatment modalities consist of the following:

Group 1: The experimental group receives a parenteral injection consisting of $1\times10^{12}$ of the anti-HDS selected lambda coliphage suspended in 0.5 cc of sterile normal saline.

Group 2: A first control group receives a parenteral injection consisting of $1\times10^{12}$ of the wild-type phage from which the Anti-HDS selected phage were developed, suspended in 0.5 cc of normal sterile saline.

Group 3: A second control group receives a parenteral injection of normal sterile saline.

Evidence that treatment with the anti-HDS selected phage prevented the development of a lethal event in the bacteremia model is measured using the following three criteria: 2
(1) Survival of the animal
(2) Bacterial counts: Samples of blood are withdrawn every ½ hour from the three groups of infected mice, and the rate of increase or decrease in *E. coli* colony counts in the three groups is noted.
(3) Phage counts: In the samples of blood withdrawn from the infected mice, the numbers of pfu of the anti-HDS selected phage and the numbers of pfu of the wild-type phage are noted.

Example 4

Genetic engineering of phage to express molecules that antagonize the host defense system, thereby enabling the phage to delay inactivation by the host defense system.

Part 1. Making the Fusion Protein

Step 1. A double-stranded DNA encoding the complement antagonizing peptide LARSNL (SEQ ID NO: 3) is synthesized on an automated oligonucleotide synthesizer using standard techniques.

Step 2. The gene for the phage coat surface protein of interest (see part 2, below) is cloned into a plasmid vector system, by techniques known in the art. The oligonucleotide that has been prepared in Step 1 is cloned into the plasmid vector system by in-frame fusion at the 3'-end of the gene for the surface protein.

Step 3. The fusion gene is then incorporated into a phage by the in vivo generalized recombination system in the host bacteria for the phage. The phage then expresses the fusion protein on its surface.

Part 2: Selecting phage coat surface proteins for fusion with the peptide/protein of interest.

A. Incorporating the gene for the complement-antagonizing peptide into a phage whose genome is well characterized The orfX gene, which encodes a carboxy-terminal tail protein of lambda coliphage, is one for which it is known that foreign nucleotide sequences can be introduced without there being disruption of the structure or function of the phage. The tail surface protein expressed by the orfX gene is made into a fusion protein with the complement-antagonizing peptide, by the plasmid vector method described in part 1 above.

B. Incorporating a gene for a complement-antagonizing peptide into a phage whose genome is not well characterized.

Step 1. Selection of the phage surface protein to be fused with the complement-antagonizing peptide:

a) Isolation of phage coat surface proteins and preparation of antibodies thereto:

(1) Samples of the phage of interest are broken up in 0.1% SDS detergent for 2 minutes at 95° C. The mixture is cooled and placed in 9M urea, and is then separated by high resolution 2 D gel electrophoresis. The protein fragments are then isolated from the gel, and processed as described below.

(2) Samples of the protein fragments from the gel are injected into animals to produce either polyclonal or monoclonal antibodies.

(3) Antibodies are isolated and then marked with uranium. These marked antibodies are reacted against whole phage. The marker pinpoints precisely those proteins on the surface of the phage to which the antibodies have bound through visualization by electronmicroscopy. [See e.g. K. Williams and M. Chase, ed., *Methods In Immunology and Immunochemistry,* Vol. 1, 1967, Academic Press.] Antibodies directed against a surface protein extending outward from the surface of the virus are retained for further use.

b) Preparation of phage restriction fragments:

The genome of the phage is cut by restriction enzymes, and the resulting restriction fragments are cloned into expression vector plasmids. Each of these plasmids expresses its corresponding protein, creating a pool of expressed proteins.

c) Reacting the expressed proteins with the marked antibodies:

The antibodies directed against a surface protein extending outward from the surface of the virus are reacted against the proteins expressed by the plasmid vectors.

d) Correlating coat protein antibodies to the plasmid vectors that express the genes for those coat proteins:

The reaction of a marked antibody with an expressed protein pinpoints the expression plasmid whose enclosed restriction fragment expresses the particular protein. Thus, the genomic fragment encoding each coat surface protein is determined using the marked antibodies.

e) Determining that the gene in its entirety has been obtained:

The restriction fragments containing a gene for a surface protein are micro-sequenced by the Sanger technique to determine (1) the precise amino acid sequence of the coat surface proteins; (2) the presence of a start and a stop signal (indicating that the gene in its entirety has been obtained); and (3) the presence of either a C-terminal or an N-terminal amino acid.

Step 2. Fusing the candidate phage surface protein with the complement-antagonizing peptide of interest:

a) Preparing the coat protein gene for fusion:

The gene for a surface protein is contained in its plasmid expression vector. The oligo-nucleotide for the complement-antagonizing peptide is spliced into this plasmid expression vector by in-frame fusion at the 3'-end of the coat surface protein.

b) Incorporating the fusion gene into the phage of interest:

The fusion gene is incorporated into the phage by the in vivo generalized recombination system in the host bacteria for the phage.

c) Demonstrating that the phage expresses the fusion protein:

The phage is incubated with a corresponding heavy metal-marked antibody that has been raised against the coat surface protein. The marker is detected on the phage by electronmicroscopy only if the phage has expressed that fusion protein on its surface. [See e.g. K. Williams and M. Chase, *Methods In Immunology and Immunochemistry,* Vol. 1, 1967, Academic Press.]

Example 5

Demonstration that the genetically engineered phage delay inactivation by the HDS, compared to wild-type phage:

Two groups of mice are injected with phage as specified below:

Group 1: The experimental group receives an IV injection consisting of $1\times10^{12}$ of the genetically modified phage, suspended in 0.5 cc of normal sterile saline.

Group 2: The control group receives an IV injection consisting of $1\times10^{12}$ of the wild-type phage from which the genetically modified phage were derived, suspended in 0.5 cc of sterile normal saline.

Both groups of mice are bled at regular intervals, and the blood samples assayed for phage content (by pfu assays) to determine the following:

1) Assays for half-lives of the two phages: For each group of mice, the point in time is noted at which there remains in circulation only half (i.e., $1\times10^6$) the amount of phage as administered at the outset. The point in time at which half of the genetically modified phage have been eliminated from the circulation is at least 15% longer than the corresponding point in time at which half of the wild-type phage have been eliminated from the circulation.

2) Assays for absolute numbers: For each group of mice, a sample of blood is taken at precisely 1 hour after administration of the phage. The criterion used is that at 1 hour post-injection, pfu assays reveal that the numbers of genetically engineered phage still in circulation in the experimental animal are at least 10% higher than the numbers of wild-type phage still in circulation in the control animal.

Example 6

Determination that the genetically engineered phage has a greater capacity than wild type phage to prevent lethal infections in mice.

Part 1. Peritonitis Model:

An $LD_{50}$ dosage of *E. coli* is administered intraperitonally (IP) to laboratory mice. The strain of *E. coli* used is one known to be lysed by the coliphage strain that has been genetically engineered. The treatment modality is administered precisely 20 minutes after the bacteria are injected, but before the onset of symptoms. The treatment modalities consist of the following:

Group 1: The experimental group receives an IP injection consisting of $1\times10^{12}$ of the genetically engineered lambda coliphage suspended in 2 cc of sterile normal saline.

Group 2: A first control group receives an IP injection consisting of $1\times10^{12}$ of the wild-type phage from which the genetically modified phage were developed, suspended in 2 cc of normal sterile saline.

Group 3: A second control group receives an IP injection of normal sterile saline.

Evidence that treatment with the genetically modified phage prevented the development of a lethal event in the peritonitis model is measured by using the following three criteria:

(1) Survival of the animal
(2) Bacterial counts: Samples of peritoneal fluid are withdrawn every ½ hour from the three groups of infected mice, and the rate of increase or decrease in *E. coli* colony counts in the three groups is noted
(3) Phage control: Using the samples of IP fluid withdrawn from the infected mice, the numbers of pfu of the genetically engineered phage versus the numbers of pfu of the wild-type phage are noted.

Part 2. Bacteremia Model:

An $LD_{50}$ dosage of *E. coli* is administered intravenously (IV) to laboratory mice, where the strain of *E. coli* used is known to be lysed by the coliphage strain that was genetically engineered. The treatment modality (see below) is administered precisely 20 minutes after the bacteria are injected, but before the onset of symptoms. The treatment modalities consist of the following:

Group 1: The experimental group receives an IV injection consisting of $1\times10^{12}$ of the genetically engineered lambda coliphage suspended in 0.5 cc of sterile normal saline.

Group 2: A first control group receives an IV injection consisting of $1\times10^{12}$ of the wild-type phage from which the genetically engineered phage were developed, suspended in 0.5 cc of sterile normal saline.

Group 3: A second control group receives an IV injection of 0.5 cc of sterile normal saline.

Evidence that treatment with the genetically engineered phage prevented the development of a lethal event in the bacteremia model is measured using the following three criteria:

(1) Survival of the animal
(2) Bacterial counts: In the samples of blood that are withdrawn every ½ hour from the three groups of infected mice, the absolute numbers as well as the rate of increase or decrease in *E. coli* colony counts is noted, for each of those three groups.
(3) Phage counts: In the samples of blood withdrawn from the infected mice, the numbers of pfu of the genetically engineered phage and the numbers of pfu of the wild-type phage are noted.

Example 7

Determination that anti-HDS selected phage specific for two types of bacteria have a greater capacity to prevent lethal infections than the wild type phage.

|  | Relevant Genotype | Source |
|---|---|---|
| Bacteria Strain Number |  |  |
| CRM 1 | *E. Coli* K12 btuB::Tn10 | NIH stock collection |
| CRM 2 | *E. coli* K12 mut D5 | NIH stock collection |
| CRM 3 | *Salmonella typhimurium* LT2 | NIH stock collection |
| Phage Strain Number |  |  |
| W60 | λcI60cY17 | Produced according to the present invention. |
| Argo1 | λcI60cY17arg1 | Produced according to the present invention. |
| Argo2 | λCI60cY17arg2 | Produced according to the present invention. |
| R34 | P22vir3 | NIH stock collection |
| Argo3 | P22vir arg3 | Produced according to the present invention. |
| Argo4 | P22vir arg4 | Produced according to the present invention. |

Part 1. Preparation of bacteria and bacteriophage stocks and detection of toxin levels in phage lysates.

*E. coli* CRM1 or *S. typhimurium* CRM3 were grown from a single colony, in 150 ml of LB medium in a shaking incubator at 37° C. until the $OD_{600}$ of the culture reached 1.0 [equivalent to $10^9$ colony forming units (cfu)]. Following growth, 100 ml of the bacterial culture was harvested by centrifugation at 16,000×g for 10 minutes at 4° C. The supernatant was discarded and the bacterial pellet resuspended in 1 ml of LB at 4° C. From this preparation the bacteria were serially diluted by a factor of 10 in PBS, from $10^{10}$ to $10^2$. Argo1 and Argo2 phage were grown in CRM1 and CRM2 host respectively, and Argo3 phage in CRM3 host, to make high titer stocks using standard procedures (Silhavy, T.J. et al., *Experiments with Gene Fusion,* Cold Spring Harbor Laboratory, Cold Spring Harbor, N.Y., 1984). Large scale preparations and purifications of bacteriophage by cesium chloride density centrifugation were performed according to Sambrook et al., 1989, Sambrook, et al., *Molecular Cloning: A Laboratory Manual, 2nd Edition,* pp. 2.73–2.81, 1989. Toxin levels in phage preparations were measured quantitatively by the Limulus Amebocyte Lysate assay (associates of Cape Cod, Inc., Woods Hole, Mass.).

Page 2. Animal model of bacterial infection.

For each infection experiment, one month old Balb/c female mice in groups of three were used. To determine the lethal dose of bacteria, serial dilutions ($10^2$–$10^{11}$ cfu) were injected intraperitoneally (IP) into mice and the animals were observed for 100 hours. In addition, to determine whether bacteria or phage injected into the peritoneal cavity can effectively enter the circulatory system, experiments were performed in which either bacteria or phage were injected IP followed by the collection of blood samples by puncturing the orbital plexus with a heparinized capillary tube. Approximately 1 ml of blood was collected into a 1.5 ml Eppendorf tube containing 10 $\mu l$ of heparin (5,000 USP units/ml). The blood samples were centrifuged at 10,000×g for 5 min and the plasma was collected with sterile pipettes. Plasma from these samples was titered for bacterial cfu and bacteriophage plaque forming units (pfu). Blood samples were also collected from these mice prior to injection of phage or bacteria to assure that animals used in these experiments were free of contaminating bacteria and phage. Mice inoculated with bacteria were scored for levels of illness by monitoring for the following symptoms (indicating progressive disease states): decreased physical activity and ruffled fur; general lethargy and hunchback posture; exudative accumulation around partially closed eyes; moribund; and finally death.

Part 3. Experiments to study the efficacy of bacteriophage as anti-bacterial agents.

Four groups of mice were infected with $2 \times 10^8$ cfu of *E. coli* CRM1 by IP injection. This dose of CRM1 is lethal for Balb/c mice. After infection, three of the groups were injected IP with $2 \times 10^{10}$ pfu of bacteriophage $\lambda$ strain W60 or the long-circulating mutants of that strain. The fourth group was monitored as an untreated control. The mice in this experiment were scored for degree of illness as described above.

Part 4. Comparison of protein profiles of wild-type $\lambda$ and $\lambda$ mutants.

Preparations of purified bacteriophage were examined by high resolution two-dimensional protein electrophoresis (Bjellqvist, B et al., *Electrophoresis,* 14, 1357–1365, 1993; Hughes, G. J. et al., *Electrophoresis,* 13, 707–714, 1992; Merril et al., *Proc. Natl. Acad. Sci. USA,* 76, 4335–4339, 1979) to search for virion protein differences between wild-type and mutant bacteriophage strains. Proteins found to vary by charge or molecular weight were partially sequenced by N-terminal sequencing (Hewick, R. M. et al., *J. Biol. Chem.,* 256, 7990–7997 (1981); Matsudaira, P., *J. Biol. Chem.,* 262, 10035–10038 (1987)). The protein sequence data were used to search the EMB1 databank to identify phage genes which code for mutant proteins. Genes coding for proteins of interest were cloned and sequenced (Sambrook, J. et al., *Molecular Cloning: A Laboratory Manual, 2nd Edition,* pp. 2.73–2.81 (1989); Scharf, S., *PCR Protocols, A Guide to Methods and Applications,* pp. 84–91 (1990)). For PCR and cloning, the two primers selected were: 5'-CCA GCG ACG AGA CGA AAA AAC G-3' and 5'-TTC AGT TGT TCA CCC AGC GAG C-3', which yield a 1545 bp product from 114 bp upstream to 84 bp downstream of the $\lambda$ E gene.

Part 5. Experimental bacteremia in mice.

The presence of *E. coli* CRM1 in the mouse circulatory system after IP injection of $10^8$ or $10^9$ bacteria was followed by sampling blood from the orbital plexus. IP injection of $10^8$ bacteria resulted in the accumulation of $6.5 \times 10^6$ bacterial cfu in the blood by 30 minutes. The cfu increased to $4.2 \times 10^7$ by 3 hrs and then decreased to $2.5 \times 10^4$ cfu by 24 hrs. Similarly, 30 minutes after IP injection of $10^9$ bacteria, blood levels of $1.7 \times 10^8$ bacterial cfu were observed. These levels rose to $7 \times 10^8$ by 3 hrs and then decreased to $2.5 \times 10^8$ by 7 hours. All of the animals in this latter group died sometime during the next 17 hours.

Part 6. Use of virulent mutants of $\lambda$ and P22.

As models of bacteriophage therapy, mice were infected with a laboratory strain of *E. coli* CRM1 or *S. typhimurium* CRM3. The corresponding phage strains specific for these two bacterial species were virulent strains containing specific mutations to assure virulence: $\lambda$vir(W60) and P22vir (R34). The use of virulent bacteriophage strains prevented survival of phage-infected bacteria as lysogens.

Part 7. Effects of bacterial debris and toxins in phage preparations.

Injection of $10^9$ pfu filter-sterilized Argo1 phage lysates made in LB broth produced only a mild clinical reaction (ruffled fur) in mice, despite an endotoxin level of $5 \times 10^4$ EU/ml in the phage preparation as determined by Limulus Amebocyte Lystate assay. In contrast, Argo3 phage lysates prepared in a similar manner on *S. typhimurium* had endotoxin levels of $5 \times 10^5$ EU/ml, and all the animals died within 12 hours after IP injection. However, cesium chloride density gradient centrifugation-purified stocks of Argo1 and Argo3, with endotoxin levels reduced to $0.3 \times 10^1$ EU/ml and $1 \times 10^3$ EU/ml, respectively, had no adverse effects at all on mice when injected IP.

Part 8. Development and partial characterization of long-circulating bacteriophage.

Bacteriophage with an enhanced capacity to avoid entrapment by the HDS were developed by selecting phage strains that could remain in the circulatory system of mice for progressively longer periods of time. This selection was started by injecting IP into each mouse $10^{11}$ pfu of $\lambda$vir (W60) grown on either wild-type CRM1 or mutator strain CRM2, followed by collection of blood samples from the mice at 7 hours. The use of the mutator *E. coli* CRM2 bacteria in one set of serial passage experiments was intended to increase the incidence of mutation in phage $\lambda$, so as to enhance the probability that one or more of the phage offspring would have properties that permit evasion of the HDS. The phage titers at 7 hours were $10^9$ and $10^8$ from the mutagenized and nonmutagenized phage, respectively. The phage titers in the circulatory system decreased to $10^2$ after 48 hours, and to undetectable levels after 120 hours. The residual phage present at 7 hours were regrown to high titers in bacteria. The regrown high-titer phage were purified by passing through a 0.22 $\mu$m GS filter. This serial passage cycle of phage injection into animals, isolation, and regrowth in bacteria was repeated nine more times. $10^{10}$ phage were injected IP in the second through the tenth cycles. Of these, only $10^6$ remained in the circulatory system at 18 hours in the second cycle, but in subsequent cycles the titers gradually rose, so that $10^9$ remained in the circulatory system at 18 hours in the 4th cycle.

Figure 1:
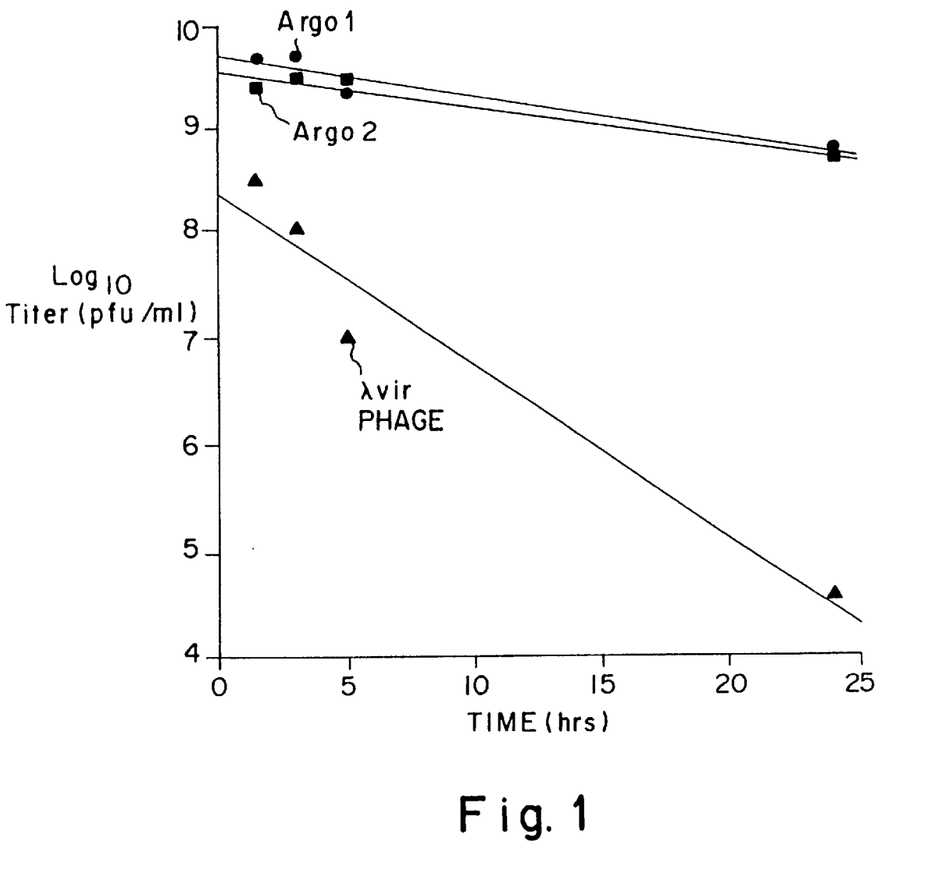
FIG. 1 shows the capacities of the selected long circulating phage Argo1 (●) and Argo2 (■) phage to remain in the mouse circulatory system following IP injection of $10^{10}$ pfu into Balb/c female mice as compared to that of the same dose of the λvir phage (▲). The data are plotted in a semi-logarithmic graph in which the logarithm of the phage titer is plotted against the time blood was sampled from the mouse circulatory system in hours. The selected long circulating mutant Argo1 and Argo2 phage display almost identical enhanced capacities to avoid RES entrapment, in comparison to their parental λvir phage. Regression analysis indicates that the capacity of Argo1 and Argo2 phage to remain in the circulatory system is significantly better ($P=0.003$) than that of the λvir phage.

The last six selection cycles provided no significant increase in the number of phage remaining in the circulatory system at 18 hours. Following the 10th cycle of the selection process, a single plaque from each of the two experiments was isolated, purified, and grown to high titers on the CRM1 host and designated as Argo1 (cycled on CRM1) and Argo2 (cycled on CRM2). Both Argo1 and Argo2 displayed similar enhanced capacity to avoid HDS entrapment. For example, the 18 hour survival after IP injection of Argo1 was 16,000-fold higher, and of Argo2 was 13,000-fold higher, than that of the parental λ strain (FIG. 1).

A similar selection process was utilized to isolate long-circulating variants of the Salmonella phage P22vir(R34). After eight selection cycles, long-circulating single phage plaques were similarly isolated and purified. Two such isolates, designated Argo3 and Argo4, were compared with P22vir for their rates of clearance from the mouse circulatory system. After an IP injection of $5 \times 10^7$ pfu, there were no detectable P22vir at 24 hours. In contrast, $3 \times 10^2$ pfu and $2 \times 10^3$ pfu of Argo3 and Argo4, respectively, were detected under the same conditions.

Part 9. Comparison of long-circulating Argo phage versus wild-type phage as antibacterial agents in an animal model.

Figure 2A:
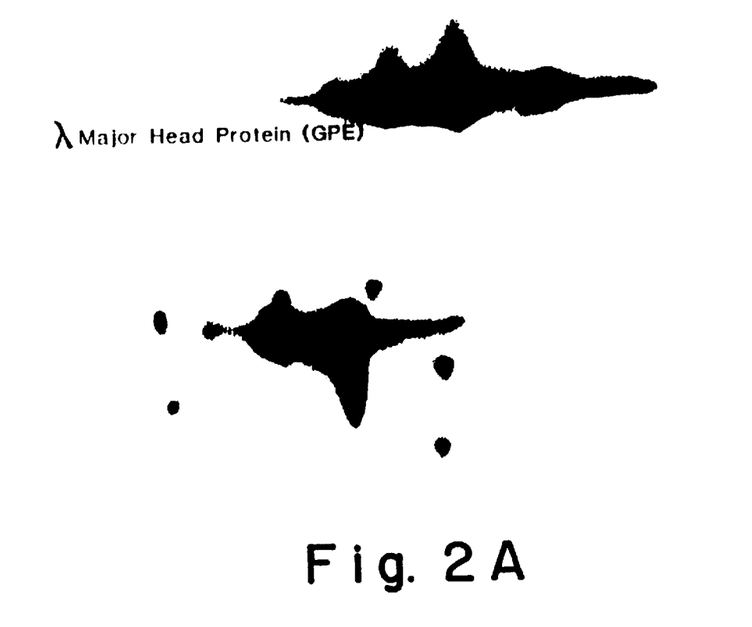
FIG. 2 shows high resolution two-dimensional protein electrophoretograms which demonstrate an alkaline shift in the charge of the 38 kD λ capsid E protein found in Argo1 versus the parental λvir phage. The electrophoretic pattern of the region of the gel containing λvir capsid E protein is illustrated in frame A. Frame B shows the same region of the electrophoretogram containing the Argo1 capsid E protein, demonstrating the alkaline shift in this protein.
Figure 2B:
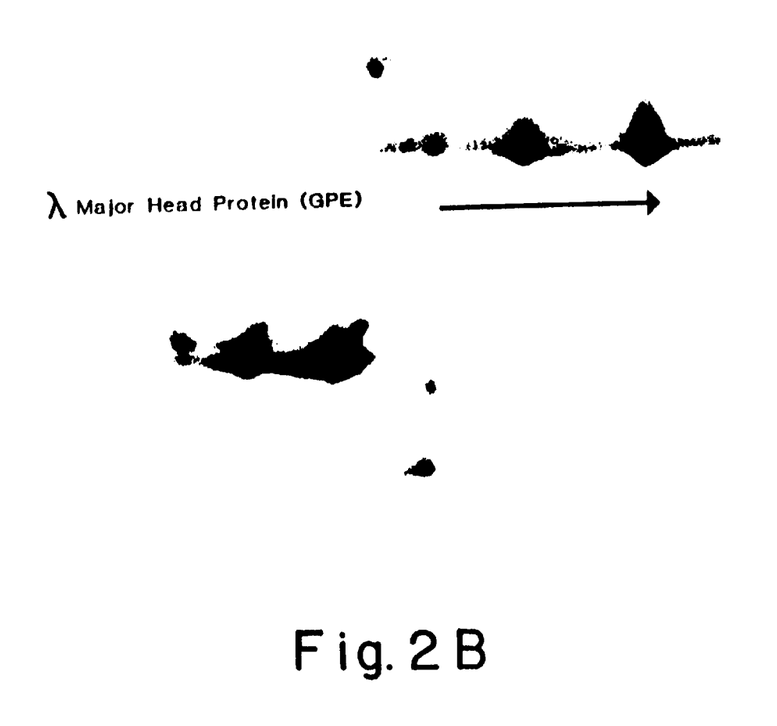

Four groups of mice were injected IP with $2 \times 10^8$ cfu of *E. coli* CRM1. The mice were scored for degree of illness as previously described. The first group was a control, with no phage treatment. Within 5 hours these mice exhibited ruffled fur, lethargy and hunchback posture. By 24 hours they were moribund, and they died within 48 hours. There were three groups treated with phage. All of the mice treated with phage survived. However, those treated with λvir (Group 2) had severe illness before finally recovering, while those treated with Argo1 (Group 3) and Argo2 (Group 4) exhibited only minor signs of illness before complete recovery (FIG. 2).

Figure 3:
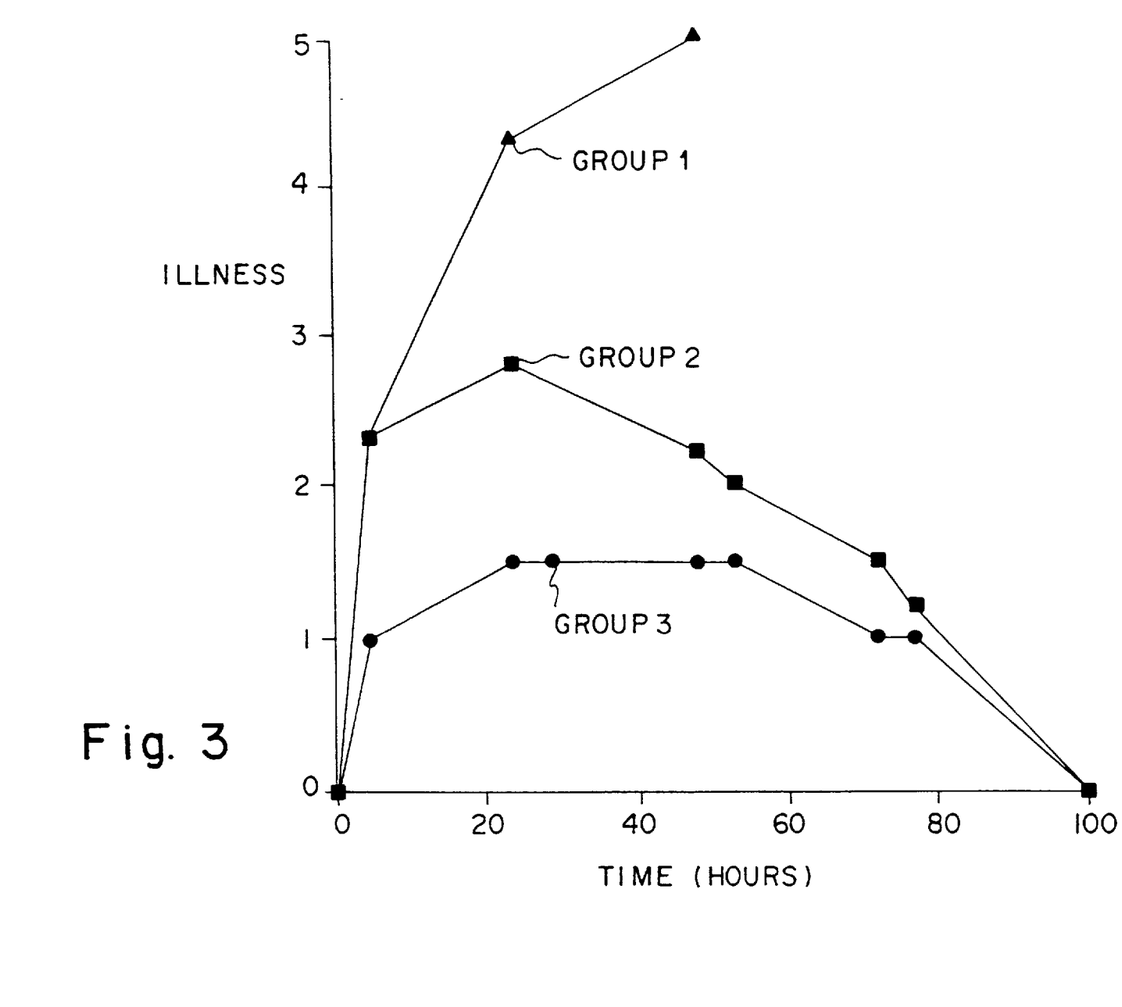

The following results show that the ability of phage to influence bacterial infections is dose-dependent. Mice were injected IP with CRM1 ($2 \times 10^8$ cfu) suspended in PBS and stored overnight. In contrast to the experiment in FIG. 2, the control group that did not receive any phage in this experiment did not die by 48 hours, an effect that was likely due to reduced virulence of the washed and refrigerated bacteria used in this experiment. However, they did develop moderately severe signs of illness. In the phage treatment groups, 30 minutes after the bacterial injection the animals received Argo1 phage in doses ranging from $10^2$ to $10^{10}$ pfu. As shown in FIG. 3, at the minimum doses of phage ($10^2$ pfu), at 30 hours after infection, the animals show illness which was only slightly reduced from that seen in the controls. With increasing doses of phage, the animals fared progressively better. At the maximum dose of phage used ($10^{10}$ pfu), the animals showed only minimal illness (decreased physical activity and ruffled fur), and these animals were nearly fully recovered at 48 hours.

Part 10. Characterization of Argo1 and Argo2 phage.

Figure 4:
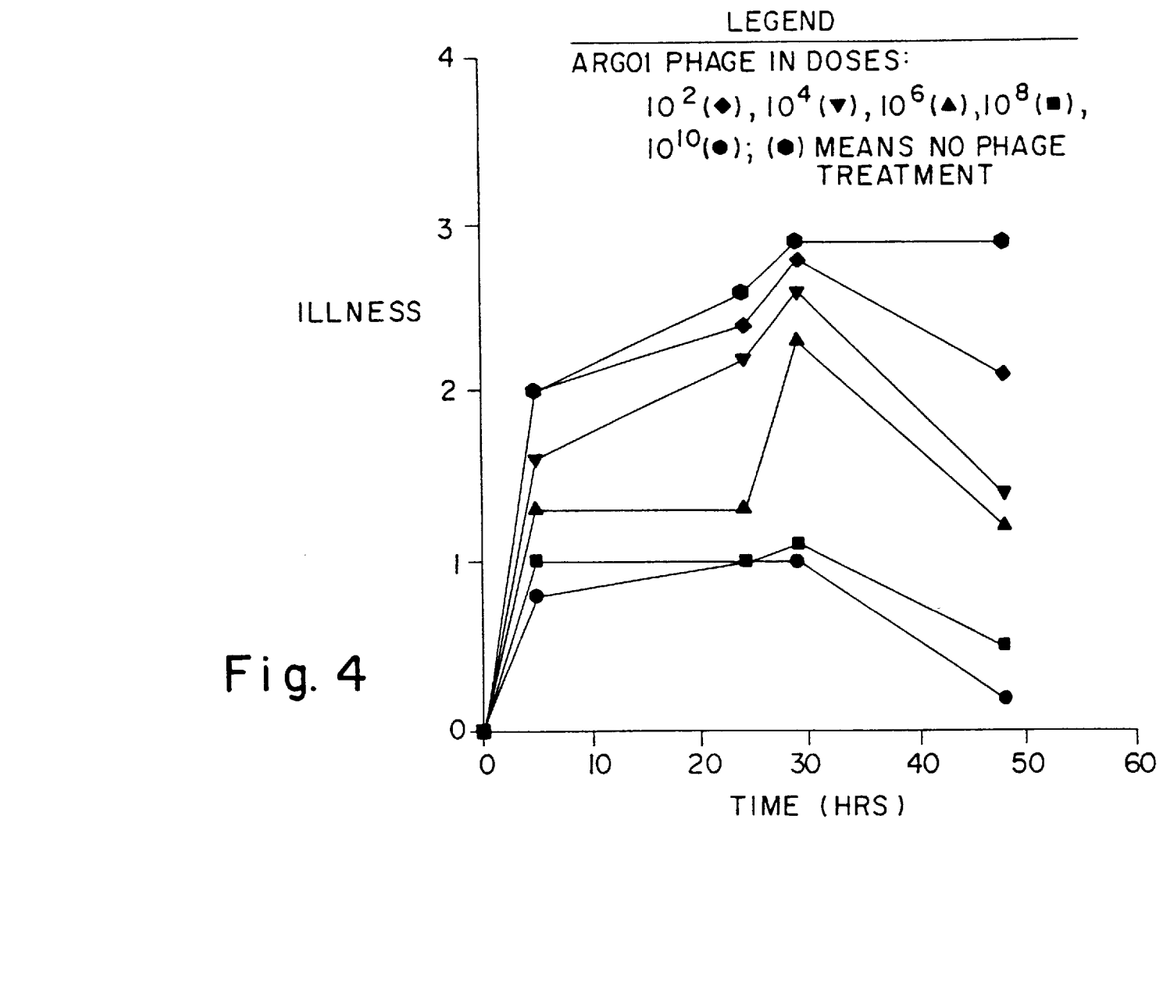
FIG. 4 shows a dose response to Argo1 phage in mice infected with *E. coli* CRM1. The experimental design is the same as that employed in FIG. 3. In the phage treatment groups, 30 minutes after the bacterial injection the animals received Argo1 phage in doses $10^2$ (♦), $10^4$ (▼), $10^6$ (▲), $10^8$ (■), $10^{10}$ (●); (●) means no phage treatment. Each experimental point represents the results with 5 animals and had a standard error of the mean of 0.2 or less.

The capsid proteins of λvir and its two Argo derivatives were analyzed by high resolution two-dimensional electrophoresis. The results revealed an alkaline shift in the 38 kD major viral protein in Argo1 compared to λvir (FIG. 4). The same electrophoretic protein shift was observed in Argo2. N-terminal amino acid sequencing of the 38 kD protein by Edman degradation showed the following sequence for the fist 15 amino acid residues for all three phage SMYTTAQL-LAANEQK (SEQ ID NO: 4). This sequence matched completely with the corresponding region of the major λ capsid head protein E (Proteete, A. R., *Bacteriophage P22, Chapter 11 in The Viruses, Vol. 2: The Bacteriophages*, pp. 683–724 (1988)). Dideoxy sequencing of the PCR amplified genes for the λ capsid E protein in Argo1 and Argo2 revealed a G-A transition mutation at nucleotide position 6606 (position 706 of SEQ ID NO: 6) in the λ capsid E gene in both Argo1 and Argo2. This transition mutation resulted in the substitution of the basic amino acid lysine for the acidic amino acid glutamic acid at position 158 of the λ capsid E protein in both Argo strains. Argo2 protein profiles displayed the presence of an additional altered protein, which also had an alkaline shift. This second protein has a molecular weight of 11.6 kD. N-terminal amino acid sequence analysis of the 11.6 kD protein in λvir and Argo2 phage showed the sequence for the first 16 residues to be: MTSKET-FTHYQPQGNS (SEQ ID NO; 5) . This sequence is identical with that of the second major capsid head protein D of λ (Daniels, D. L. et al., *Lambda II, pp.* 519–676 (1983)). The DNA sequence alteration in the D gene of Argo2 was not determined.

It is noteworthy that while Argo1 was the result of spontaneous mutation and Argo2 was isolated after mutagenesis, both contained an identical mutation in the λ capsid E protein showing the change of glutamic acid to lysine, presumably at the solvent-exposed surface of the phage virion. While the long-circulating Argo2 phage had an additional mutation in the capsid D protein, the presence of a common alteration in the E protein in both of the long-circulating phage strains indicates that the change in the capsid E protein is the major factor in diminishing phage entrapment by the RES.

As will be evident from the foregoing, the invention provides, as specific embodiments thereof, long-lasting or long-circulating purified or toxin-free mutants or variants of *E. coli* phage λ and of *S. typhimurium* phage 22. The foregoing also illustrates that the long-circulating, purified mutants or variants of the *E. coli* and of the *S. typhimurium* phage have greater capability as antibacterial agents than the corresponding parental strain in animals infected with lethal doses of respective bacteria. However, while *E. coli* and *S. typhimurium* phage have been used to illustrate the invention, those skilled in the art will appreciate that the invention is broadly applicable to long-circulating, purified mutants or variants of bacteriophage in general, it being understood that, for present purposes, the references to "long-lasting" or "long-circulating" are intended to mean variants which have at least a 15% longer half-life in an animal's circulatory system, than the corresponding wild-type phage.

---

We claim:

1. A method for amplifying a gene coding for a capsid E protein which enables a phage to have at least a 15% longer half-life in an animal's circulatory system than a corresponding wild-type phage, comprising the steps of;

isolating long-circulating bacteriophage, wherein said bacteriophage has at least a 15% longer half-life in an animal's circulatory system than a corresponding wild-type phage, and selectively amplifying a gene from said bacteriophage using at least one of the following primers;

5'-CCA GCG ACG AGA CGA AAA MC G-3' (SEQ ID NO:1)

5'-TTC AGT TGT TCA CCC AGC GAG C-3' (SEQ ID NO;2), wherein said bacteriophage is λvir and wherein a G nucleotide is replaced by an A nucleotide at position 706 (SEQ ID NO: 6) which results in glutamic acid being replaced by lysine within the E capsid protein.

2. A primer for amplifying a gene coding for a protein which enables a phage to have at least a 15% longer half-life in an animal's circulatory system than a corresponding wild-type phage, wherein said primer is selected from the group consisting of 5'-CCA GCG ACG AGA CGA AAA MC G-3' (SEQ ID NO: 1) AND 5'-TTC AGT TGT TCA CCC AGC GAG C-3' (SEQ ID NO: 2).

3. A bacteriophage with a modified capsid protein, wherein a G nucleotide is replaced by an A nucleotide at position 706 (SEQ ID NO: 6) which results in glutamic acid being replaced by lysine within the capsid protein, and wherein said modified capsid protein results in a bacteriophage with at least a 15% longer half-life in an animal's circulatory system than a corresponding wild-type phage, wherein said bacteriophage is λvir and said capsid protein is λ capsid E protein.

4. A pharmaceutical composition comprising, a purified bacteriophage having at least a 15% longer half-life in an animal's circulatory system than the corresponding wild-type phage, and a pharmaceutically acceptable carrier, wherein said bacteriophage is λvir and wherein a G nucleotide is replaced by an A nucleotide at position 706 (SEQ ID NO: 6) which results in glutamic acid being replaced by lysine within the E capsid protein.

* * * * *